(12) United States Patent  
Lieberman et al.

(10) Patent No.: US 6,714,711 B1  
(45) Date of Patent: Mar. 30, 2004

(54) OPTICAL WAVEGUIDE ILLUMINATOR

(75) Inventors: Robert A. Lieberman, Torrance, CA (US); Edgar A. Mendoza, Redondo Beach, CA (US); Yevgeniy Durets, Long Beach, CA (US)

(73) Assignee: Optech Ventures, LLC, Torrance, CA (US)

( * ) Notice: Subject to any disclaimer, the term of this patent is extended or adjusted under 35 U.S.C. 154(b) by 0 days.

(21) Appl. No.: 09/685,387

(22) Filed: Oct. 10, 2000

Related U.S. Application Data

(63) Continuation-in-part of application No. 09/334,845, filed on Jun. 16, 1999, now Pat. No. 6,205,263.

(51) Int. Cl.[7] .............................. G02B 6/02; G02B 6/18
(52) U.S. Cl. ...................... 385/124; 385/901; 362/552
(58) Field of Search ............................. 385/147, 901, 385/124; 362/31, 551, 552, 558, 582

(56) References Cited

U.S. PATENT DOCUMENTS

| | | | | |
|---|---|---|---|---|
| 5,845,038 A | * | 12/1998 | Lundin et al. | 385/901 |
| 5,905,837 A | * | 5/1999 | Wang et al. | 385/123 |
| 6,169,836 B1 | * | 1/2001 | Sugiyama et al. | 385/123 |

* cited by examiner

*Primary Examiner*—Mark A. Robinson  
*Assistant Examiner*—Alessandro Amari  
(74) *Attorney, Agent, or Firm*—Lawrence S. Cohen

(57) ABSTRACT

Methods and apparatus for producing an optical waveguide illuminator are disclosed. By controlling the propagation of light in the core and cladding regions of the waveguide, distributed light emission along a length of an optical fiber or along a planar waveguide surface can be achieved by varying the core/cladding refractive index ratio and introducing light scattering centers in the core.

7 Claims, 6 Drawing Sheets

VARIABLE CORE/CLADDING REFRACTIVE INDEX RATIO

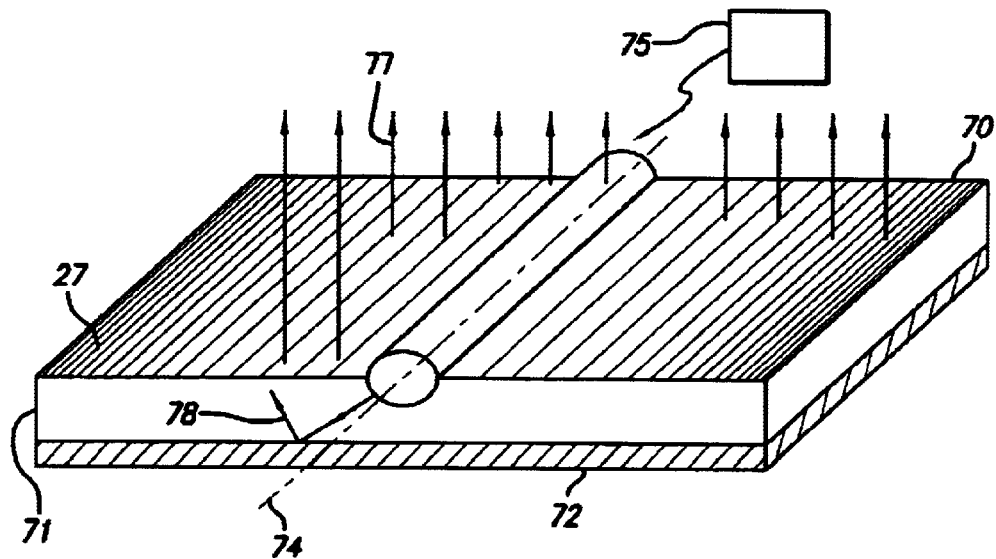
FIG. 7
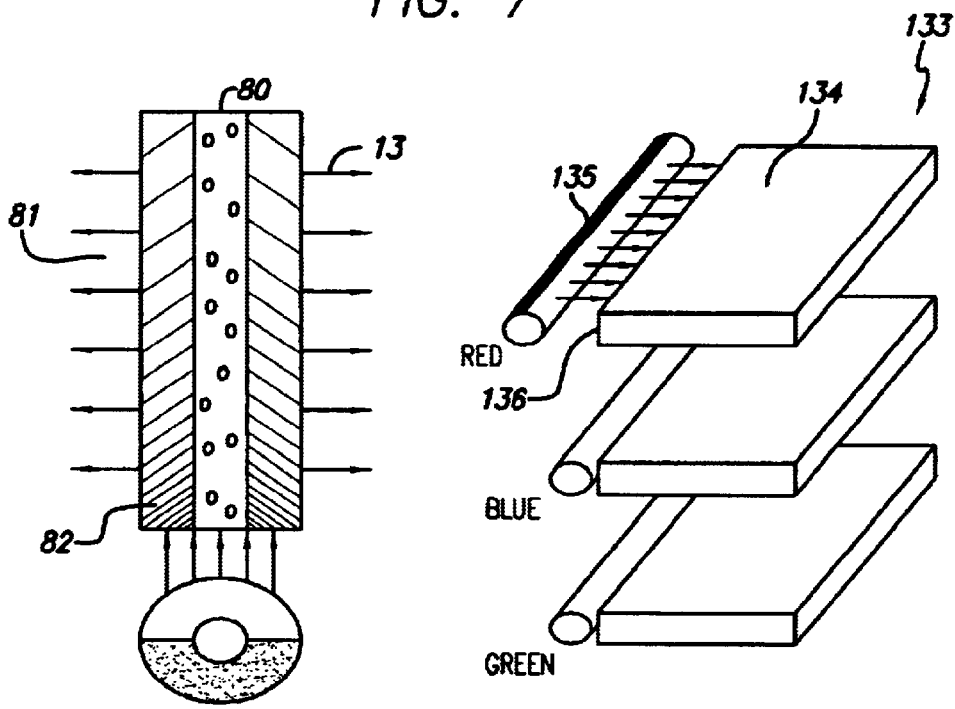
FIG. 8
FIG. 9

OPTICAL WAVEGUIDE ILLUMINATOR

CROSS-REFERENCE TO RELATED APPLICATIONS

The present application is a Continuation-in-Part of patent application Ser. No. 09/334,845 now U.S. Pat. No. 6,205,263, filed Jun. 16, 1999 and assigned to the assignee of the present application, the content of which is incorporated herein by reference provided as Attachment A hereto.

FIELD OF THE INVENTION

The present invention relates generally to the propagation and emission of light in optical fibers and more particularly to methods for controlling illumination in light emitting optical waveguides and to waveguides in which controlled illumination occurs.

BACKGROUND OF THE INVENTION

Optical fibers are being used with increasing regularity in sensor applications as described, for example, in U.S. Pat. No. 4,834,496 issued May 30, 1989 to Lee L. Blyler, Jr., et al. which discloses distributed fiber optic chemical sensors. Such sensors comprise an optical fiber with a core and a cladding that is permeable. The cladding, or a coating on the cladding, includes a composition, the optical properties of which are altered in the presence of a material to be detected. The light (i.e. the wavelength or the intensity of the light) transmitted through the core of the fiber is a function of the change in optical properties caused by the interaction of a composition included in the permeable cladding or coating with the material to be detected. The change in optical properties may comprise (for example) a change in the index of refraction (or indices of refraction differential), or an increase or decrease in the optical absorbance or fluorescence of the composition.

The above noted copending application describes techniques for controlling the power dissipated in an optical fiber in order, for example, to provide a loss-compensated distributed sensor where the sensitivity of the fiber is linear throughout its length.

Typically, an optical fiber, having a core and a surrounding cladding, is designed to transmit and contain light within the fiber core. Light escaping from the core is considered an undesirable characteristic, as it creates a loss of power or the ability to carry information. In other applications, as in the copending application referred to above, light which travels out of the core through the cladding can be exploited for sensor applications.

BRIEF SUMMARY OF THE INVENTION

The present invention refers to that discovery that an optical fiber can be designed with light emission properties, suitable for illumination, in a manner to produce light distributed along the fiber length or in a pattern of discrete segments at intervals along the fiber length.

The present invention describes methods for controlled light emission in an optical fiber or optical waveguide assembly to produce specified illumination patterns. Such patterns include distribution along a fiber length, or a selected pattern of discrete segments of distributed light at intervals along the fiber length. A pattern along a fiber length may be, for example, uniform or may vary according to a selected variation.

The invention is based on the realization that the characteristics of light transmitted through an optical fiber can be modified by changing, for example, the refractive index ratio and/or the absorption and scattering coefficients of the core and cladding of the fiber to control the fiber's light emission characteristics to allow the emission of light for illumination purposes.

In one embodiment of the invention, light emission is controlled by changing the core/cladding refractive index differential, also referred to as the ratio, along the length of a fiber and by inducing light scattering centers within the fiber core.

In another embodiment of the invention, distinctive light patterns are created along the fiber by introducing scattering centers such as reflective or refractive light scattering particles or voids so that light is emitted only in selected length segments.

In another embodiment of the invention, light emission along the length of a fiber is controlled by changing the core/cladding refractive index differential and by deforming the normally smooth surface texture of the fiber core/cladding boundary to promote radial light leakage.

In another embodiment of the invention, the diameter of the fiber core is changed along the length of the fiber and the core is interspersed with refractive or reflective light scattering particles or voids to promote light emission.

In another embodiment of the invention, the fiber is fabricated with a decreasing absorption coefficient core or cladding and a textured core/cladding boundary to promote light emission.

In another embodiment of the invention, the diameter of the fiber core is increased along the length of the fiber and the core/cladding boundary is texturized to promote light emission.

In another embodiment of the invention, the fiber is fabricated with a decreasing absorption coefficient core or cladding and the core is interspersed with refractive or reflective light scattering particles to promote light emission.

In another embodiment of the invention, the fiber includes a reflective surface to backscatter light emitted longitudinally from the fiber.

In another embodiment of the invention the core and/or cladding of an optical fiber is mechanically scribed in a variable pitch spiral configuration to promote light emission. The pitch can be selected to provide uniform light emission along the length of the fiber.

In another embodiment of the invention, the refractive index of a glass or plastic slab is incrementally changed and scattering centers are introduced to produce an illumination plate.

In another embodiment of the invention, an illumination fiber is imbedded in a glass or plastic slab having a varying refractive index to produce an illumination plate.

In another embodiment of the invention, a slab type core with distributed light scattering centers is sandwiched between two cladding layers having varying refractive indices to provide a bi-directional light emission plate.

In another embodiment of the invention, illuminator sheets with different colored light sources are arranged in a multi-color array.

In another embodiment of the invention, multiple light-emitting fibers are distributed along a planar sheet to provide an illuminator panel.

In another embodiment of the invention, integrated optic waveguides are distributed along a planar sheet to provide an illuminator panel.

These and other embodiments of the invention will become apparent in the following description.

BRIEF DESCRIPTION OF THE DRAWINGS

FIG. 7 is a view of an imbedded fiber sheet illuminator;

FIG. 8 is a view of a two-sided sheet illuminator;

FIG. 9 is an illustrative view of a colored illuminator sheet array;

DETAILED DESCRIPTION OF THE INVENTION

For illumination applications, in one embodiment, it is advantageous to have an optical fiber exhibit a length-invariant response to transmitted light so that the distribution of light is uniform along a fiber length. Optical fibers, however, are typically characterized by transmission losses that cause the intensity of light to vary along the length of the fiber. In other embodiments, the light distribution may desirably be non-uniform according to a selected variation. In yet another embodiment, the light may be emitted in a pattern of discrete segments at intervals along the fiber length. Therefore, control of the light emission is required to achieve these embodiments.

In accordance with the principles of the invention, in one embodiment, a loss-compensated distributed optical fiber can be constructed by changing the loss mechanism characteristics of the fiber whereby the intensity of light emitted by the fiber is uniform along the fiber length. As indicated in the above noted copending application, several techniques may be used to obtain distributed light intensity along an optical fiber, including:

a) increasing the core/cladding refractive index ratio
b) increasing the core diameter
c) increasing the absorption coefficient of the cladding
d) increasing the scattering coefficient of the core In addition, a number of methods have been developed to scratch, abrade, chemically deform, remove, or otherwise disturb portions of the cladding so that light traveling down the length of the fiber is emitted through deformities in the cladding. One such technique is described in U.S. Pat. No. 5,042,892 where light is allowed to escape from the core by partially or completely removing regions of the cladding. Fibers constructed using this method, however, are difficult to fabricate and do not provide controlled emission.

One embodiment of an optical fiber for transmitting and radially emitting light comprises an inner core of transparent glass or plastic material and a surrounding outer cladding material. The fiber is fabricated with a varying core/cladding refractive index ratio. The fiber also has scattering centers in the core to cause light to be scattered to promote distributed light emission.

When light energy is introduced at the input end of the fiber by a light source, the transmitted light strikes the core scattering centers and scattered light rays are refracted or reflected at the core/cladding interface, as is known in the art. In accordance with Snell's Law of Refraction, for angles of incidence greater than the critical angle, total reflection of the cladding incident rays takes place within the core. For angles of incidence less than the critical angle however, the rays are refracted in the cladding.

Figure 1:
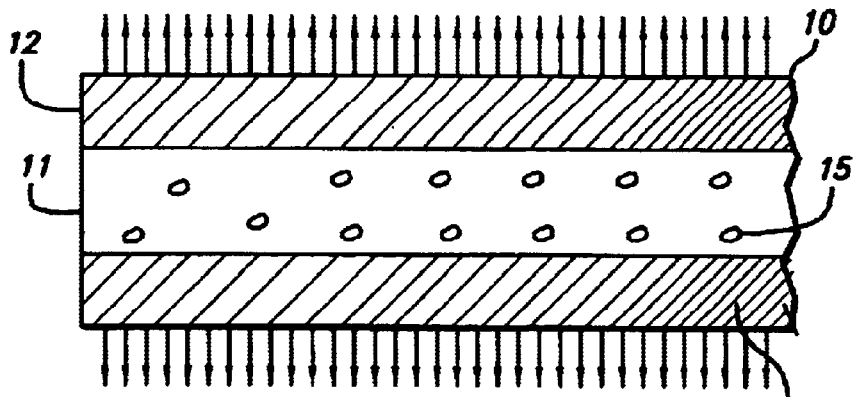
FIG. 1 is a partial sectional view of an illumination optical fiber.
Figure 2:
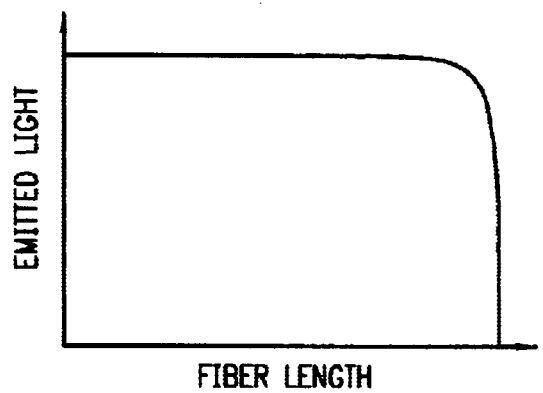
FIG. 2 is a power distribution curve of light emission along a fiber in accordance with the principles of the invention.

With reference to FIG. 1, a distributed illumination optical fiber 10 having a core 11 and a surrounding cladding 12 emits light when the fiber is fabricated with a variable core/cladding refractive index ratio along the length of the fiber and the core is interspersed with refractive and/or reflective light scattering centers 15. A first approximation equilibrium mode for the distributed illumination fiber can be established when the refractive index ratio and scattering center distribution parameters are changed in a manner so that light is emitted as shown by the power distribution curve of FIG. 2. The light scattering centers can be in the form of particles or voids or other scattering means. This embodiment provides uniform illumination along a fiber length.

Figure 3:
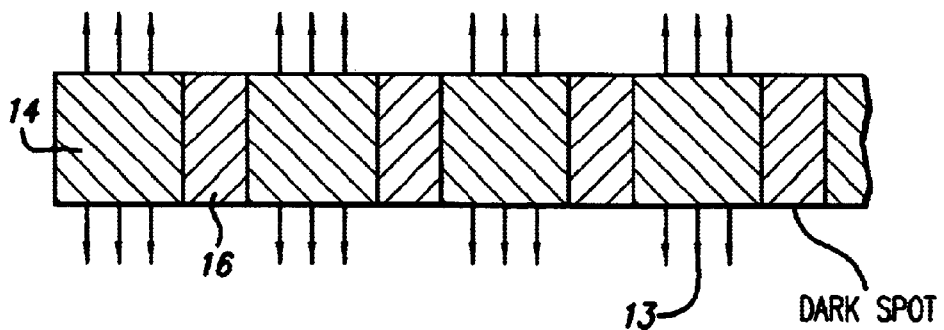
FIG. 3 is a partial sectional view of an illumination fiber with distributed scattering center regions in accordance with the principles of the invention.

FIG. 3 shows diagrammatically another embodiment of the invention where the fiber is constructed to emit a pattern of discrete light segments 13 at intervals along the fiber length. In this embodiment, the core/cladding refractive index ratio at the selected dark segments 16 is increased to create dark spots and is decreased in selected segments 14 to promote emission. The fiber may also have scattering centers distributed throughout the core or selectively in the areas of desired decreased refractive index ratio in order to increase the level of emission in those selected areas. If it is desired that the areas of increased emission 14 provide uniform levels of illumination along the fiber length, then the refractive index ratio at successive segments 14 should vary accordingly. If scattering centers are used, their concentration should be varied to promote uniform illumination at successive segments. Alternatively, such uniform illumination can be achieved by one of the other means for varying emission as described herein. Similarly, the illumination at the segments 14 can be made non-uniform in selected patterns by use of the means described herein for varying emission.

Figure 4:
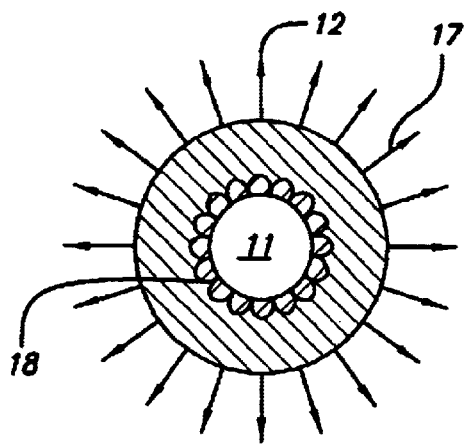
FIG. 4 is an end view of a light-emitting optical fiber using cladding deformation to promote light emission.

FIG. 4 shows an end view of another embodiment of a light emitting optical fiber 17 using interfacial light leakage to promote emission. The fiber may have selected varying or non-varying desired illumination patterns along the fiber length.

Figure 5:
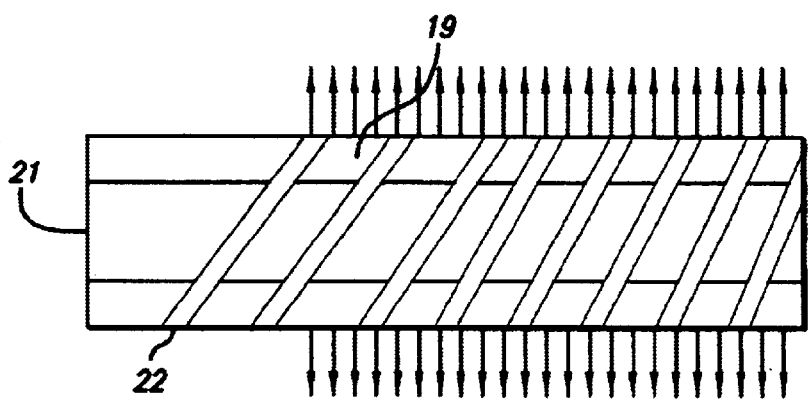
FIG. 5 is an illustration of a distributed optical fiber scribed for light emission.

The light-emitting characteristics of an optical fiber can be controlled by scribing the core and/or cladding. With reference to FIG. 5, the fiber core 21 and/or cladding 22 is shown scribed in a spiral configuration with a linearly increasing variable pitch 19 to produce uniform illumination along the fiber length. A non-uniform variation in illumination can be achieved by an appropriate variation in the pitch.

Figure 6:
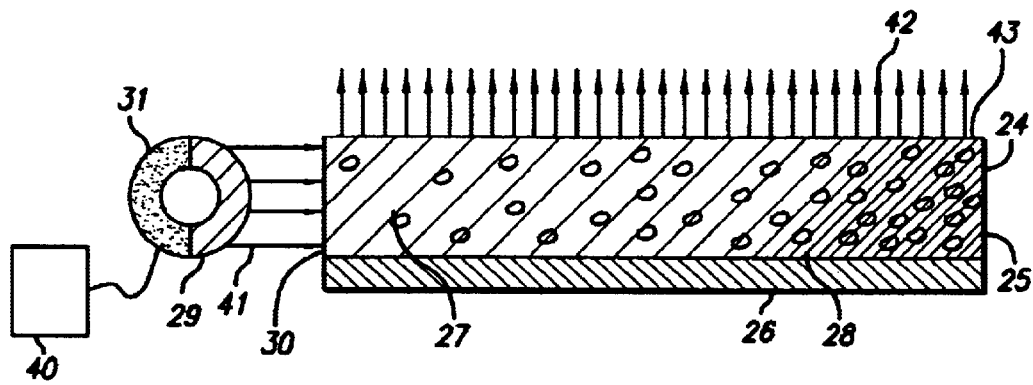
FIG. 6 is a view of an edge-fed planar sheet illuminator apparatus.

FIG. 6 shows a sheet illuminator panel structure 24 encompassing the features of the invention. The illuminator is fabricated with a slab type core 25 and a cladding 26 on one side. The core 25 has a varying refractive index, represented by the varying density lines 27, along the length of the slab structure and distributed light scattering centers 28 within the core 25 for light emission. An illumination fiber 29 connected to a light source 40 is used to inject light 41 along an edge 30 of the core 25. A reflective cladding layer 26 redirects scattered light rays toward the light-emitting surface of the core 25. The fiber 29 has a reflective cladding layer portion 31 to direct emitted light rays toward the edge 30 of the waveguide. The refractive index 27 and distribution of scattering centers 28 are increased linearly across the core 25 so that evenly distributed light 42 escapes from the light-emitting surface 43.

A sheet illuminator panel with an imbedded illumination fiber encompassing the features of the invention is shown in FIG. 7. The panel 70 is fabricated with a slab type core 71 and a reflective cladding layer 72. An illumination fiber 73 is imbedded along a central axis 74 in the core 71 and is connected to an external light source 75. The core 71 is designed with a linearly increasing refractive index, represented by the varying density lines 27, extending from the fiber 73 bilaterally from the central axis 74 to provide distributed light emission 77. The reflective cladding layer 72 redirects any scattered light rays 78 toward the core surface.

As shown in FIG. 8, another embodiment of the invention has a slab type core 80 sandwiched between two cladding layers 81 for bidirectional illumination. The cladding layers 81 are designed with a linearly increasing refractive index, represented by the varying density lines 82, to provide distributed light emission 13.

With reference to FIG. 9, the features of the invention can be embodied in an array of edge-fed planar illumination sheets 133 for color blending applications. The planar sheets 133 are constructed with colored surface layers 134 or illuminated by colored fibers 135 having a reflective cladding to direct emitted light rays toward the edge of the sheets 136.

Figure 10:
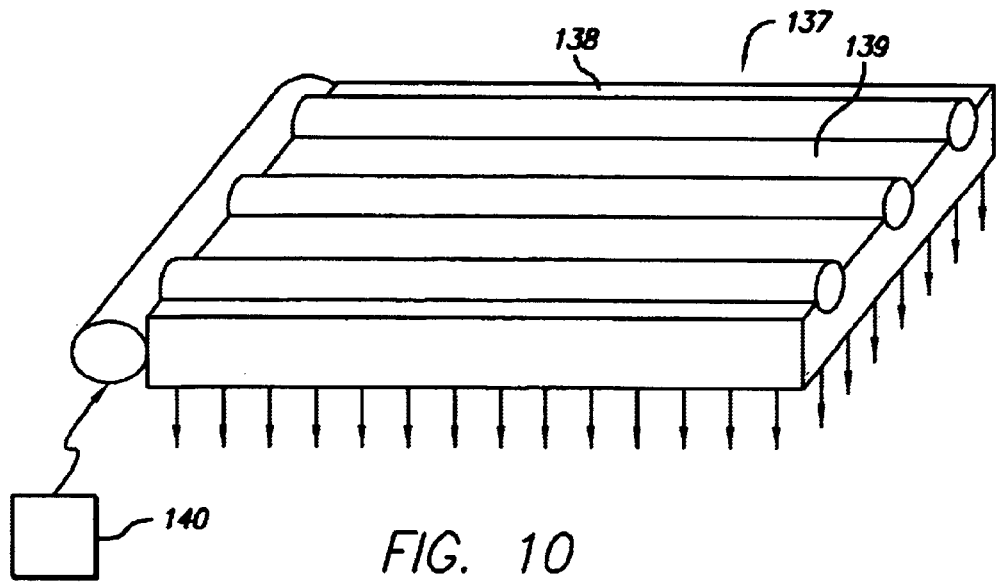
FIG. 10 is an illustrative view of a ceiling illuminator panel.

FIG. 10 shows a type of ceiling illuminator panel 137 using a plurality of illuminating fibers 138 distributed along a slab sheet layer 139 and fed by a distributed emission optical fiber light source 140.

Figure 11:
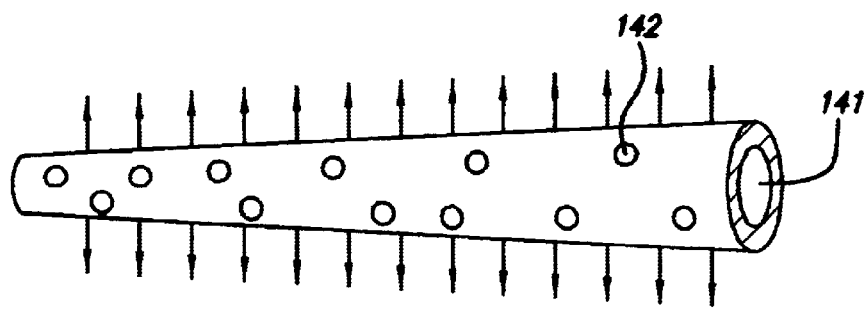
FIG. 11 is an illustrative view of a fiber illuminator with a varying diameter core.

FIG. 11 shows an illustrative embodiment of the invention where the diameter of the fiber core 141 is changed along the length of the fiber, the light source being at the smaller end, and the core is interspersed with refractive or reflective light scattering centers 142 to promote distributed light emission.

Figure 12:
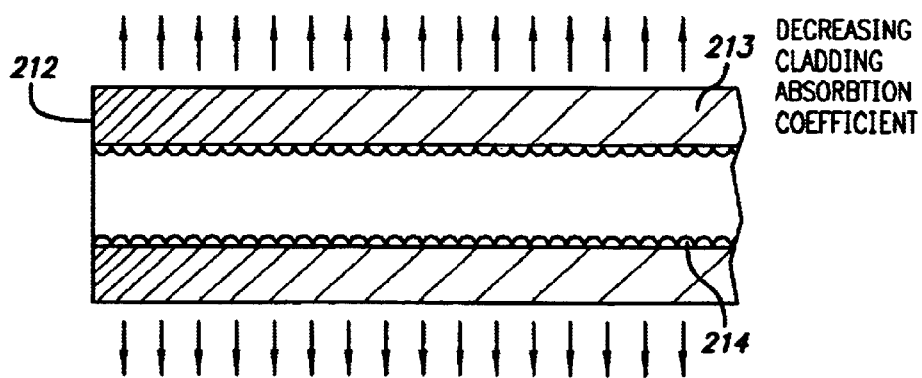
FIG. 12 is a view of a fiber illuminator with a varying absorption coefficient cladding and a textured core/cladding boundary.

FIG. 12 shows an embodiment of the invention where the fiber cladding 212 is fabricated with a decreasing absorption coefficient, represented by lines of varying density 213, and the core/cladding boundary 214 is textured to promote light emission.

Figure 13:
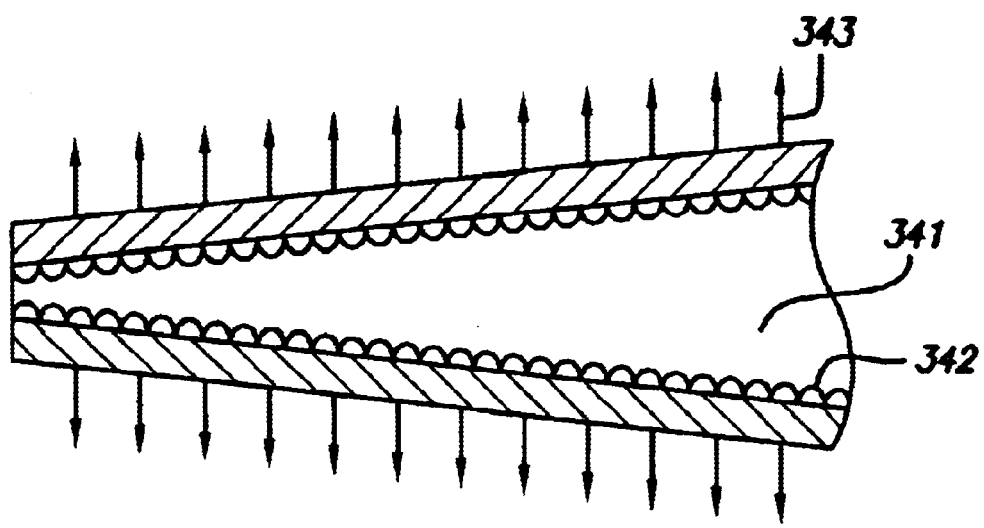
FIG. 13 is a view of a fiber illuminator with a varying diameter core and a textured core/cladding boundary.

FIG. 13 shows another embodiment of the invention where the core diameter 341 along the length of the fiber is increased, the light source being at the smaller end, and the core/cladding boundary 342 is textured to promote light emission 343.

Figure 14:
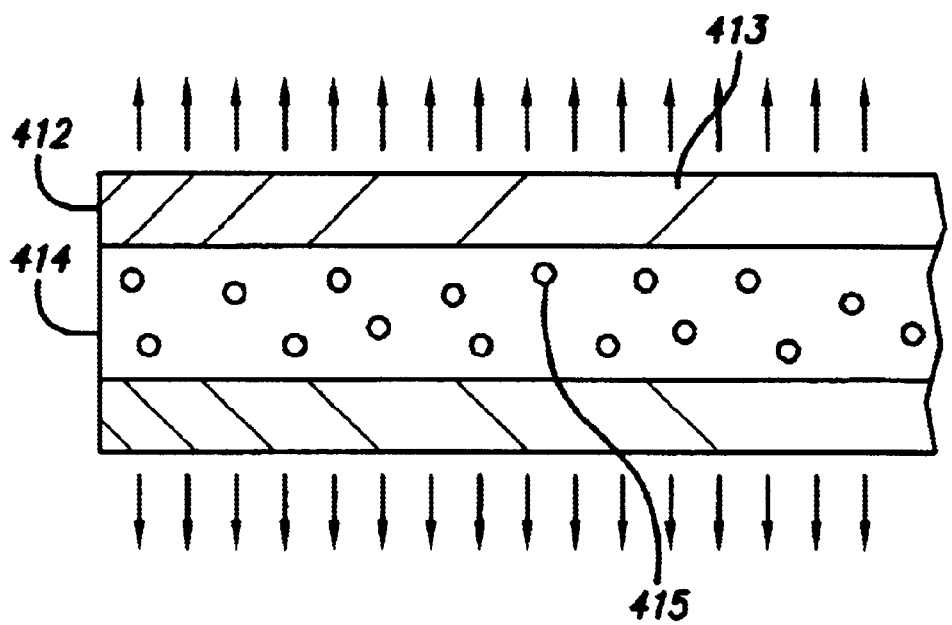
FIG. 14 is an illustrative view of a fiber illuminator with a varying absorption coefficient cladding and distributed light scattering centers in the core.

FIG. 14 shows an embodiment of the invention where the fiber cladding 412 has a decreasing absorption coefficient, represented by lines of varying density 413, and the core 414 is interspersed with refractive and/or reflective light scattering centers 415 to promote light emission.

Figure 15:
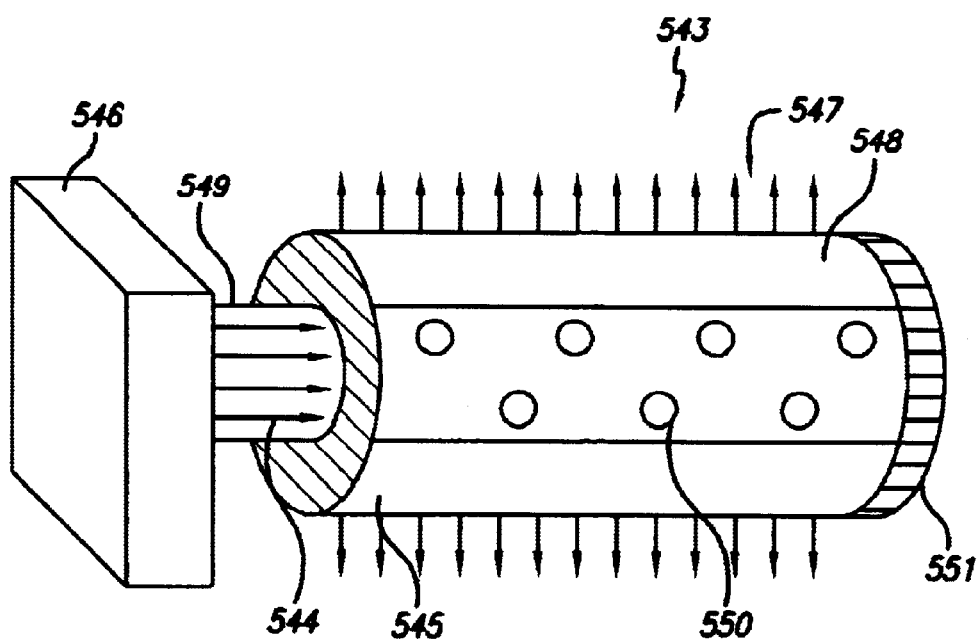
FIG. 15 is a view of an illumination fiber apparatus in accordance with the principles of the invention.

FIG. 15 shows an apparatus of the invention 543 where light energy 544 is introduced at the input end of the fiber 545 by a light source 546 and radially emitted light 547 is propagated along the fiber length. The fiber cladding is fabricated with a material 548 whose refractive index varies along its length and the fiber core 549 is interspersed with light scattering centers 550 which may be particles of glass or plastic, air bubbles or the like. The output end of the fiber has a reflective surface 551 to backscatter any light emitted longitudinally from the fiber.

Figure 16:
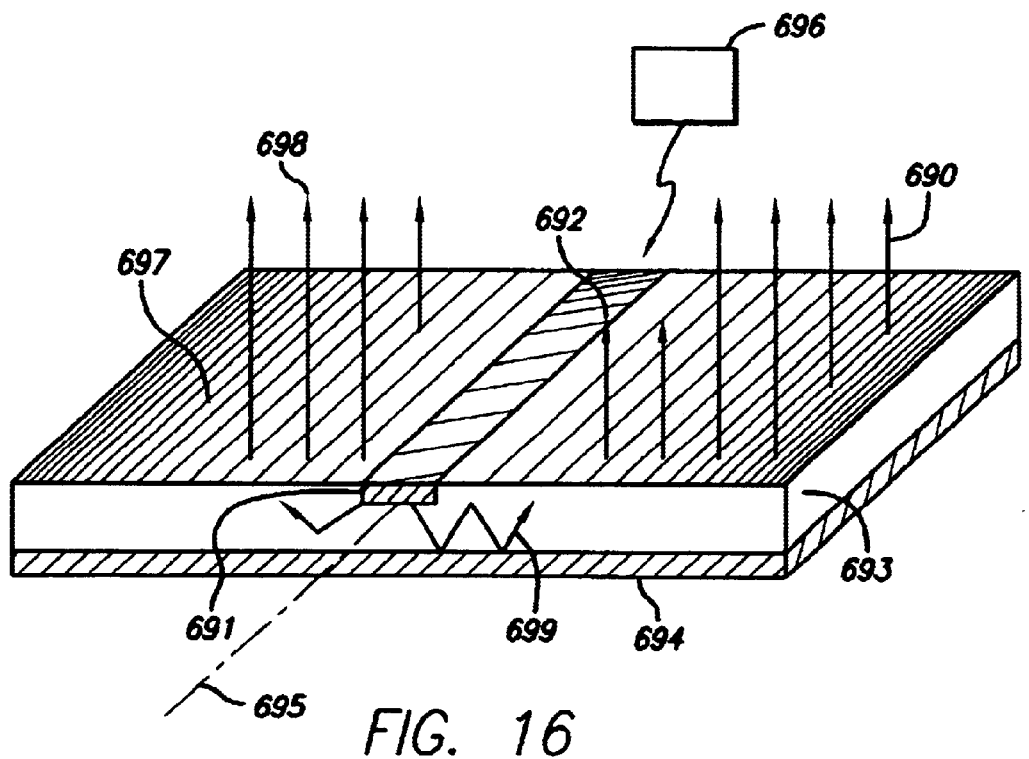
FIG. 16 is a view of a planar sheet illuminator using integrated optic waveguides.

FIG. 16 shows a sheet illuminator 690 encompassing the features of the invention with an imbedded integrated optic waveguide 691. The illuminator 690 is fabricated with a slab type core 693 and a reflective cladding layer 694. The integrated waveguide 691 is imbedded along a central axis 695 in the core 693 and is fabricated with a varying refractive index, represented by lines of varying density 692, for light distribution. The waveguide 691 is connected to an external light source 696. The core 693 is designed with a linearly increasing refractive index, represented by lines of varying density 697, extending bilaterally from the central axis 695 to provide light emission 698. The reflective cladding layer 694 redirects any scattered light rays 699 toward the core surface.

Although the various features of novelty that characterize the invention have been described in terms of certain preferred embodiments, other embodiments will become apparent to those of ordinary skill in the art, in view of the disclosure herein. Accordingly, the present invention is not intended to be limited by the recitation of the preferred embodiments, but is instead intended to be defined solely by reference to the appended claims.

What is claimed is:

1. A method for controlling the propagation and emission of light in an optical fiber waveguide having a light transmitting fiber core and one or more light emitting mechanisms, comprising the steps of varying at least one parameter of said light transmitting fiber core and at least one parameter of at least one of said light emitting mechanisms in a manner to control the intensity of radially emitted light along the fiber length wherein said light transmitting fiber core parameter is the fiber core/cladding refractive index ratio and said light emitting mechanism is light scattering centers and the light emitting mechanism parameter is the light scattering centers distribution within the fiber core.

2. A method for controlling the propagation and emission of light in an optical fiber waveguide having a light transmitting fiber core and one or more light emitting mechanisms, comprising the steps of varying at least one parameter of said light transmitting fiber core and at least one parameter of at least one of said light emitting mechanisms in a manner to control the intensity of radially emitted light along the fiber length wherein said light transmitting fiber core parameter is a decreasing fiber core/cladding refractive index ratio along first selected lengths of the fiber and an increasing fiber core/cladding refractive index ratio along second selected lengths of the fiber and said light emitting mechanism is light scattering centers and the light emitting mechanism parameter is the light scattering centers distribution within the fiber core, said parameters varying in a manner to provide radially emitted light along said first selected lengths of the fiber and dark regions along said second selected lengths of the fiber.

3. A method for controlling the propagation and emission of light in an optical fiber having a light transmitting fiber core by varying at least one parameter of the light transmitting fiber core in a manner to control the emission of radially emitted light along the fiber length for illumination wherein said at least one parameter is the core/cladding refractive index ratio and further wherein said optical fiber also has one or more light emitting mechanisms at least one of which is light scattering centers and said method includes varying at least one parameter of said light scattering centers and said at least one parameter is the light scattering centers distribution within the core.

4. A light-emitting optical waveguide for illumination comprising a light transmitting core and one or more light emitting mechanisms said light transmitting core having at least one variable parameter and said light emitting mechanisms having at least one variable parameter of at least one of said light emitting mechanisms for controlling the characteristics of light propagating along the waveguide in a manner to emit light from the waveguide surface wherein said light transmitting core parameter is a varying core/cladding refractive index ratio and said light emitting mechanism is light scattering centers and the light emitting mechanism parameter is the light scattering centers distribution within the core.

5. The light-emitting optical waveguide of claim 4 wherein the light scattering centers distribution within the core deflects light propagating through said core to an angle less than a critical angle which is associated with total internal reflection within said optical waveguide.

6. The light-emitting optical waveguide of claim 4 wherein said light-transmitting core is a fiber and said light transmitting core parameter is a varying core/cladding refractive index ratio and said light-emitting mechanism is distributed light-scattering centers within said core and the light emitting mechanism parameter is the light scattering centers distribution within the core whereby light propagating through said core is defected to an angle less than a critical angle which is associated with total internal reflection within said optical waveguide.

7. A light-emitting optical fiber comprising an optical fiber waveguide having a light transmitting fiber core configured to vary the core/cladding refractive index ratio along a selected length of the fiber and one or more light emitting mechanisms comprising light scattering centers having varying distribution within the fiber core along said selected length of the fiber to control the characteristics of light propagating through the fiber core whereby light is radially emitted along the selected length of the fiber.

* * * * *